United States Patent [19]

Hay

[11] 4,291,689

[45] Sep. 29, 1981

[54] EVACUATION MANIFOLD FOR MEDICAL ANESTHESIA CIRCUITS

[75] Inventor: Wayne W. Hay, Madison, Wis.

[73] Assignee: Airco, Inc., Montvale, N.J.

[21] Appl. No.: 86,962

[22] Filed: Oct. 19, 1979

[51] Int. Cl.³ .............................................. A61M 16/00
[52] U.S. Cl. ........................... 128/200.24; 128/204.18; 128/205.24; 128/205.19; 128/910
[58] Field of Search .............. 128/910, 205.19, 204.18, 128/200.24, 205.24; 137/493.9

[56] References Cited

U.S. PATENT DOCUMENTS

| | | | |
|---|---|---|---|
| 1,617,711 | 2/1927 | Hennebohle | 137/493.9 |
| 1,620,720 | 3/1927 | Buck | 137/493.9 |
| 4,180,066 | 12/1979 | Milliken et al. | 128/910 X |

FOREIGN PATENT DOCUMENTS 676479 7/1952 United Kingdom ............. 137/493.9

*Primary Examiner*—Henry J. Recla

*Attorney, Agent, or Firm*—Roger M. Rathbun; Larry R. Cassett

[57] ABSTRACT

A manifold is described for use with anesthesia breathing circuits and which is adapted to receive exhaust anesthetic gases from the anesthesia breathing circuit for disposal thereof. The manifold is connectible to a vacuum system for such disposal and includes a needle valve which may be set to establish a desired flow of exhaust anesthetic gas to the vacuum system. Because the pressures (either positive or negative) within the manifold will also have an effect on pressures within the anesthesia breathing circuit from which the exhaust anesthetic gas is received, it is necessary to control the pressure inside the manifold within certain predetermined limits. Relief valves are thus provided and which relieve the pressure within the manifold at certain predetermined positive and negative limits. The relief valves are so arranged that both may be opened manually by a common member which is accessible exterior of the manifold and can readily be displaced by personnel. The displacement simultaneously opens both valves to free the same from sticking.

4 Claims, 1 Drawing Figure

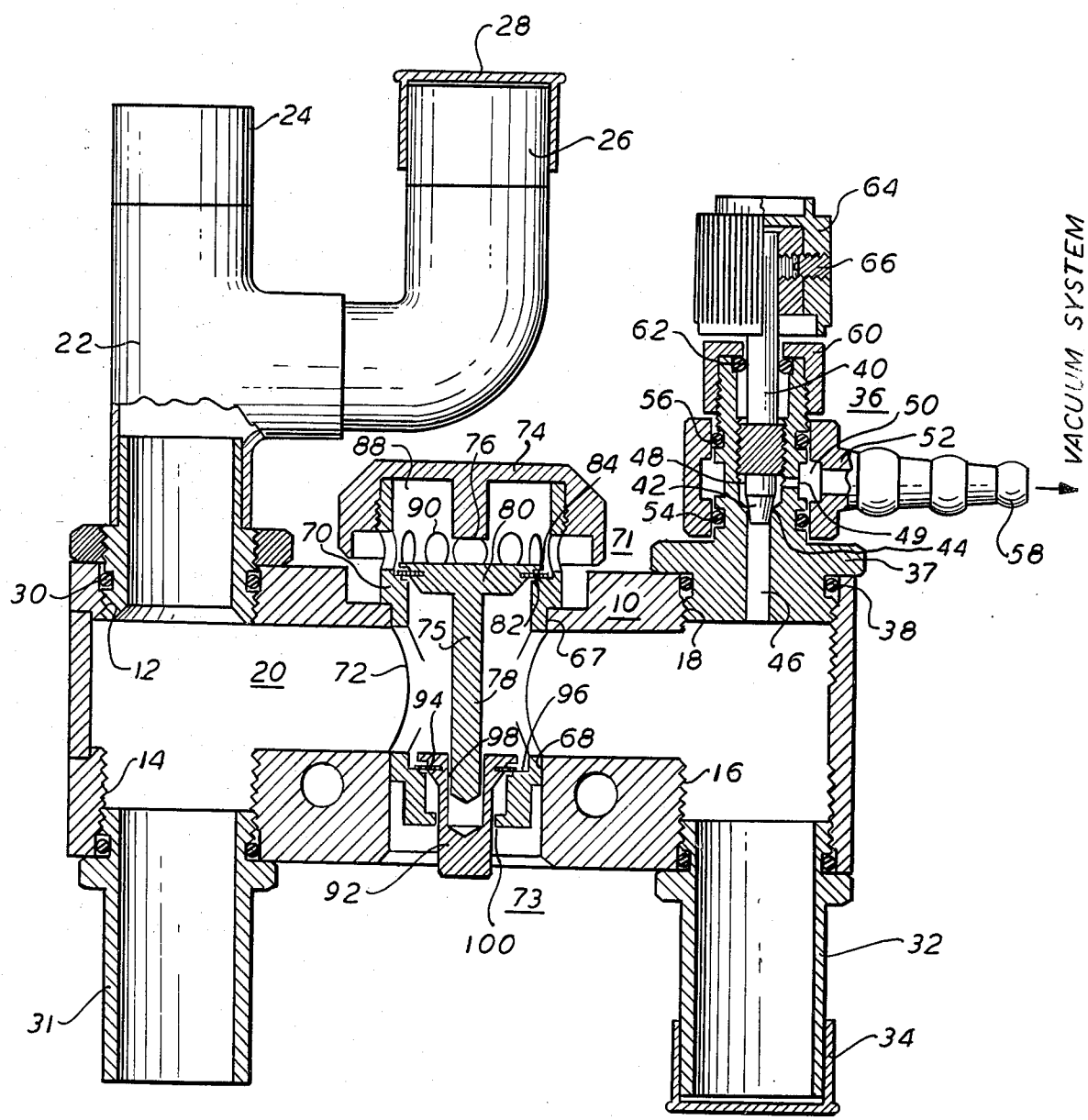

4,291,689

EVACUATION MANIFOLD FOR MEDICAL ANESTHESIA CIRCUITS

BACKGROUND OF THE INVENTION

This invention relates to a manifold which is adapted to receive exhaust anesthetic gases from an anesthesia breathing circuit and which thereafter provides control for the same to be delivered to a vacuum exhaust system.

Due to the potential harmful effects on doctors and other attending personnel in the operating theatre, anesthetic gases are, to the extent possible, eliminated from the atmosphere where such personnel are working. Typical systems include manifolds that may surround normal pop-off valves in the anesthesia breathing circuit and which carry the anesthetic gases that escape when the pop-off valve is open to some exhaust means, such as the normal hospital vacuum system, or to specially installed evacuation systems.

In order to directly connect such manifolds or other exhaust means of anesthesia machines to hospital vacuum systems, it is necessary to have some flow control valve to prevent the vacuum system from affecting the anesthesia breathing circuit pressures, and it is also normal to have some type of reservoirs due to the intermittent nature of the exhaust gas flow. The flow control valve combined with a reservoir means allows a fairly steady flow of anesthetic gases to the vacuum system and evens off the otherwise intermittent high flow and then no flow conditions of the gas from the anesthesia breathing circuit.

Accordingly, there are interposed between the various means of collecting the exhaust anesthetic gases and the vacuum systems, manifolds having valves such as needle valves, and which also contain pressure relief valves to prevent an adverse effect on the anesthesia breathing circuit itself.

One common difficulty in present manifolds is that, due to the sensitive nature of such pressure relief valves, they often encounter sticking and do not function at the proper positive or negative pressure. In the event of sticking, it is generally inconvenient to reach the stuck valve to release the same and may require the need to disassemble individual valves to free the movable valve components in separate positive pressure and negative pressure relief valves.

SUMMARY OF THE INVENTION

The manifold of the present invention is adapted to receive waste anesthetic gas from an anesthesia breathing circuit and includes a needle valve means for control of the gas before it is introduced to a hospital vacuum system. In addition, the manifold includes both a positive pressure relief valve and a negative pressure relief valve which have their valve stems interrelated such that an external member is provided which may be displaced and which thereby simultaneously displaces the stems of both the positive and negative relief valves so that both valves can be positively freed from sticking easily and conveniently without disassembly of individual valves.

DETAILED DESCRIPTION OF THE DRAWING

The invention is diagrammatically illustrated by way of example, in the drawing appended hereto, in which the FIGURE is a side view partially in section, of the manifold of the present invention.

DESCRIPTION OF THE PREFERRED EMBODIMENT

In the FIGURE herein, a side view, partially in cross-section, the manifold 10 is shown having four identical threaded sockets 12, 14, 16 and 18 and an internal chamber 20. One of the sockets 12 has threadedly engaged thereto a Y-connector 22 which has two inlets 24 and 26 for receiving excess exhaust anesthetic gas from an anesthesia breathing circuit.

Both inlets 24 and 26 are provided in the event the waste anesthetic gas is received from more than one relief valve or other means venting the anesthetic gases from the anesthesia breathing circuit. If only one such relief valve is being utilized in the anesthesia breathing circuit, one of the inlets 24 or 26 may be closed by means such as a cap 28 shown covering inlet 26. An O-ring 30 seals the Y-connector 22 to the threaded socket 12.

Each of the threaded sockets 14 and 16 of manifold 10 has threadedly fitted thereon, connectors 31 and 32, respectively. The uses of the connectors 31 and 32 are the same and both are provided for the convenience of having a different physical location for each of the connectors 31 and 32.

As shown, connector 32 is covered by a cap 34 and the description will be with respect to connector 31. The connector 31 is adapted to receive a reservoir means such as an inflatable bag to receive and inflate when an amount of exhaust anesthetic gases enters the manifold 10 in excess of the amount that can be passed on to the hospital vacuum system in the same interval, as will be later explained.

A needle valve 36 is threaded into the remaining threaded socket 18 and has a valve body 37 sealed thereagainst by means of O-ring 38. The needle valve 36 has a threaded stem 40 within valve body 37 and a tapered tip 42 which is movable with respect to valve seat 44 at the end of the needle valve inlet 46. As the valve stem 40 is rotated, therefore, the tapered tip 42 moves further into or out of the valve seat 44 to control the flow of gas entering the valve inlet 46 to the valve chamber 48 and which, in turn, communicates through hole 49 with an outer chamber 50 formed in an annular ring 52. The annular ring 52 is sealed against the valve body 37 by O-rings 54 and 56. Extending from the annular ring 52 is a connector 58 which is adapted to be connected to a suitable tubing which, in turn, connects to the hospital vacuum system.

A nut 60 is threadedly engaged to valve body 37 and retains the threaded stem 40 and seals the same by means of O-ring 62. A knob 64 is affixed to the end of the threaded stem 40 by means such as set screw 66 for turning the threaded stem 40 to adjust flow through needle valve 36.

As described, therefore, the needle valve 36 controls the flow of the exhaust anesthetic gas from the internal chamber 20 within manifold 10 to the hospital vacuum system. By adjusting the needle valve 36, a fixed flow can be established that should be at least equal to the average rate of delivery of waste or excess anesthetic gas delivered to the manifold 10. Since such is based on an average flow rate, the reservoir means, attached to threaded connector 31 fills as the delivery rate to manifold 10 exceeds the flow from manifold 10 into the vacuum system and empties as the delivery rate of anesthetic gases into manifold 10 is less than the flow into the vacuum system through needle valve 36.

The manifold 10 also has two holes 67,68 oppositely disposed with respect to each other. A sleeve 70 sealed into the openings 67 and 68 has an opening 72 therethrough which corresponds roughly to the internal chamber 20 of manifold 10. The sleeve 70 serves to locate oppositely disposed relief valves, as shown, a positive pressure relief valve 71 and a negative pressure relief valve 73.

Taking first the positive pressure relief valve 71, a cap 74 is threadedly engaged to the upper end of the sleeve 70 and has a downwardly projecting stop 76. A movable valve member 75 fits within the sleeve 70 and has a valve portion 80 of flat circular configuration and which has an outside diameter slightly greater than the inner diameter of the upper valve seat 82 formed in sleeve 70. A valve stem 78 depends downwardly from the valve portion 80. An elastomeric ring 84 is fitted to the valve portion 80 and, when valve portion 80 is in its lowermost position, the ring 84 abuts the upper valve seat 82, thus closing the upper positive pressure relief valve 71 and preventing flow from chamber 20 to chamber 88 beneath cap 74 at less than a predetermined pressure differential.

The valve stem 78 and valve body 80 thus form the gravity-loaded positive relief valve 71 having a movable valve member 75 that moves upwardly when the pressure within manifold 10 exceeds that in chamber 88 by a predetermined amount. The gas within manifold 10 is thus vented into the chamber 88 beneath cap 74 and passes out to the atmosphere through a plurality of holes 90 in the sleeve 70.

Similarly, the negative pressure relief valve has a movable valve member comprising a cup-like stem 92 which seats by means of an elastomeric ring 94 against a lower valve seat 96 formed in the sleeve 70, thus forming a gravity-loaded negative pressure relief valve. Thus, as the pressure within the manifold 10 becomes negative of a predetermined minimum value, the cup-shaped stem 92 is lifted from the lower valve seat 96, and allows air at atmospheric pressure into the manifold 10 until the gravity-loaded negative pressure relief valve again closes.

The cup-like stem 92 has a recess 98 formed therein of sufficient size as to receive the lower end of the valve stem 78 of the positive pressure relief valve 71 and is substantially coaxial therewith. As shown, there is sufficient clearance between the outside diameter of valve stem 78 and the internal diameter of recess 98 as to form a freely sliding fit therebetween.

The lower end of the cup-like stem 92 projects through the lower end of sleeve 70 and is centered in the sleeve 70 by a clearance hole 100 in the bottom end of the sleeve 70.

In operation, the double relief valve provides both gravity-loaded positive and negative pressure relief valves. The proportions of the valve stem 78 and cup-like stem 92 are such that the valve stem 78 will elevate to prevent an increase in positive pressure within manifold 10 beyond a predetermined limit without affecting the cup-like stem 92 and, in turn, the cup-like stem 92 will elevate to prevent an increase in negative pressure beyond a predetermined limit without affecting the valve stem 78. Thus the valve arrangement provides a different pressure limit for both positive and negative pressures.

Both the valve stem 78 and the cup-like stem 92 may, however, be simultaneously manually elevated from their seats 82 and 96, respectively, by a finger lifting the cup-like stem 92 from below as it projects outside the manifold 10. By this simple means, it is easy to restore both the positive and negative relief valves to effective operation in the event they become stuck in position due to prolonged idleness.

It will be understood that the scope of the method and product of this invention is not limited to the particular steps or materials disclosed herein, by way of example, but only by the scope of the appended claims.

I claim:

1. An anesthetic gas evacuation manifold, said manifold having an inlet for receiving exhaust anesthetic gases and an outlet for discharging said gases to a vacuum collection system, said manifold having a positive pressure relief valve and a negative pressure pressure relief valve, said positive pressure relief valve having a first valve seat and a first normally closed movable valve member, said first movable member adapted to move from said first valve seat when a predetermined positive pressure occurs within said manifold, said negative pressure relief valve having a second valve seat and a second normally closed movable valve member, said second movable valve member adapted to move from said second valve seat when a predetermined negative pressure occurs within said manifold and means external of said manifold to simultaneously manually move said first and second movable valve members, respectively, from said first and second valve seats.

2. An anesthetic gas evacuation manifold as defined in claim 1 wherein said first movable valve member is generally coaxially aligned with said second movable valve member.

3. An anesthetic gas evacuation manifold as defined in claim 1 wherein said first movable valve member includes a depending projecting stem, said second movable valve member has a cup-shaped stem, said depending projecting stem adapted to slidingly interfit with said cup-shaped stem, whereby said external means moves said second valve member which thereby moves first valve member.

4. An anesthetic gas evacuation manifold as defined in claim 1 wherein said first and second valve members are gravity biased to said closed positions.

* * * * *